(12) United States Patent
Anakwenze

(10) Patent No.: US 11,357,497 B1
(45) Date of Patent: Jun. 14, 2022

(54) SURGICAL SHEATH, STAPLE, AND SCAFFOLD BONE ANCHOR DEVICES

(71) Applicant: Oke A Anakwenze, Raleigh, NC (US)

(72) Inventor: Oke A Anakwenze, Raleigh, NC (US)

( * ) Notice: Subject to any disclaimer, the term of this patent is extended or adjusted under 35 U.S.C. 154(b) by 0 days.

(21) Appl. No.: 17/535,337

(22) Filed: Nov. 24, 2021

Related U.S. Application Data

(63) Continuation-in-part of application No. 17/332,612, filed on May 27, 2021, which is a continuation-in-part of application No. 15/973,303, filed on May 7, 2018, now Pat. No. 11,045,190.

(60) Provisional application No. 63/224,287, filed on Jul. 21, 2021.

(51) Int. Cl.
*A61B 17/04* (2006.01)
*A61B 17/064* (2006.01)
*A61F 2/08* (2006.01)
*A61B 17/068* (2006.01)

(52) U.S. Cl.
CPC ...... *A61B 17/0401* (2013.01); *A61B 17/0487* (2013.01); *A61B 17/0642* (2013.01); *A61F 2/0811* (2013.01); *A61B 17/04* (2013.01); *A61B 17/064* (2013.01); *A61B 17/068* (2013.01); *A61B 2017/0462* (2013.01); *A61F 2/08* (2013.01); *A61F 2002/0864* (2013.01); *A61F 2220/0016* (2013.01)

(58) Field of Classification Search
CPC . A61B 17/04; A61B 17/0401; A61B 17/0487; A61B 17/0488; A61B 17/064; A61B 17/0642; A61B 17/0644; A61B 17/068; A61B 17/0682; A61B 17/072; A61B 2017/07214; A61B 2017/0477; A61F 2/08; A61F 2/0811; A61F 2220/0016; A61F 2002/0864
USPC .......... 227/19, 175.1, 176.1; 606/1, 75, 139, 606/151, 219
See application file for complete search history.

(56) References Cited

U.S. PATENT DOCUMENTS

| | | | | |
|---|---|---|---|---|
| 4,586,502 A | * | 5/1986 | Bedi | A61B 17/068 606/151 |
| 5,328,077 A | * | 7/1994 | Lou | A61B 17/0642 227/19 |
| 5,354,292 A | * | 10/1994 | Braeuer | A61F 2/0063 606/1 |
| 5,718,706 A | * | 2/1998 | Roger | A61F 2/0811 606/86 R |
| 5,941,439 A | * | 8/1999 | Kammerer | A61B 17/068 227/67 |
| 6,059,787 A | * | 5/2000 | Allen | A61B 17/0642 606/75 |

(Continued)

*Primary Examiner* — Scott A Smith
(74) *Attorney, Agent, or Firm* — Leavitt Eldredge Law Firm

(57) ABSTRACT

A surgical bone sheath staple device, anchor, and/or scaffold enables low impact installation of distal end members in bones to secure soft tissue and the like via a deployment system. The bone sheath staples, anchors, and scaffolds secure soft tissue to bone to ensure tailored fixation of soft tissue to bone. The bone staples, anchors, and scaffolds integrate sheath and suture tightening members to secure soft tissue to bone and tailor compression of soft tissue to bone to encourage healing. The bone staples, anchors, and scaffolds integrate sheaths and suture to define attachment mechanisms and other features that secure the staples, anchors, and/or scaffolds to bone.

6 Claims, 14 Drawing Sheets

(56) References Cited

U.S. PATENT DOCUMENTS

| | | | | |
|---|---|---|---|---|
| 6,193,733 B1* | 2/2001 | Adams | A61B 17/1285 | 606/151 |
| 6,554,852 B1* | 4/2003 | Oberlander | A61B 17/0401 | 606/232 |
| 7,749,250 B2* | 7/2010 | Stone | A61B 17/0469 | 606/232 |
| 8,235,995 B2* | 8/2012 | Focht | A61B 17/068 | 606/75 |
| 8,579,909 B2* | 11/2013 | Burkus | A61B 17/025 | 606/86 A |
| 8,668,718 B2* | 3/2014 | Euteneuer | A61B 17/0644 | 606/219 |
| 8,679,123 B2* | 3/2014 | Kinmon | A61B 17/0642 | 606/75 |
| 9,033,201 B2* | 5/2015 | Euteneuer | A61B 17/0642 | 606/139 |
| 9,107,661 B2* | 8/2015 | Euteneuer | A61B 17/56 | |
| 9,271,726 B2* | 3/2016 | Euteneuer | A61B 17/0642 | |
| 9,370,356 B2* | 6/2016 | Euteneuer | A61B 17/0682 | |
| 9,585,656 B2* | 3/2017 | Taber | A61B 17/0682 | |
| 10,123,796 B2* | 11/2018 | Westling | A61B 17/0642 | |
| 11,045,190 B1* | 6/2021 | Anakwenze | A61B 17/0401 | |

\* cited by examiner

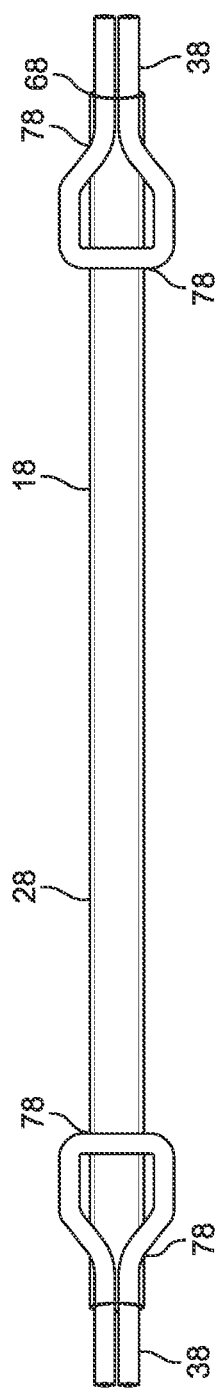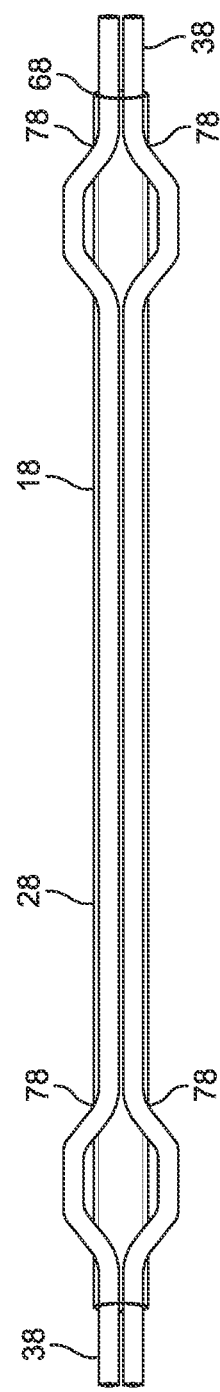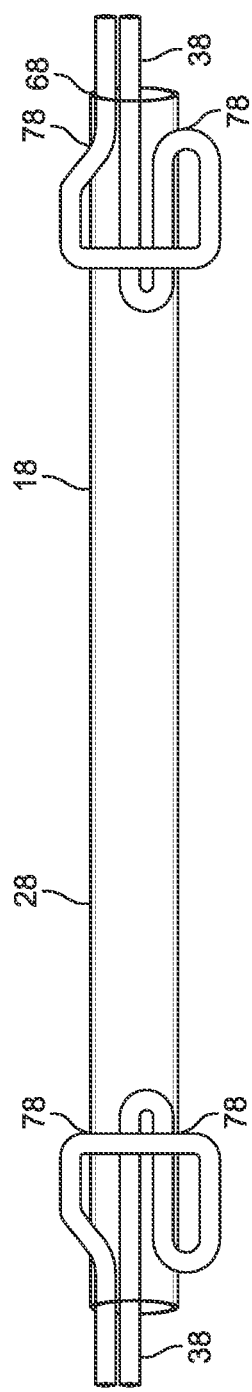

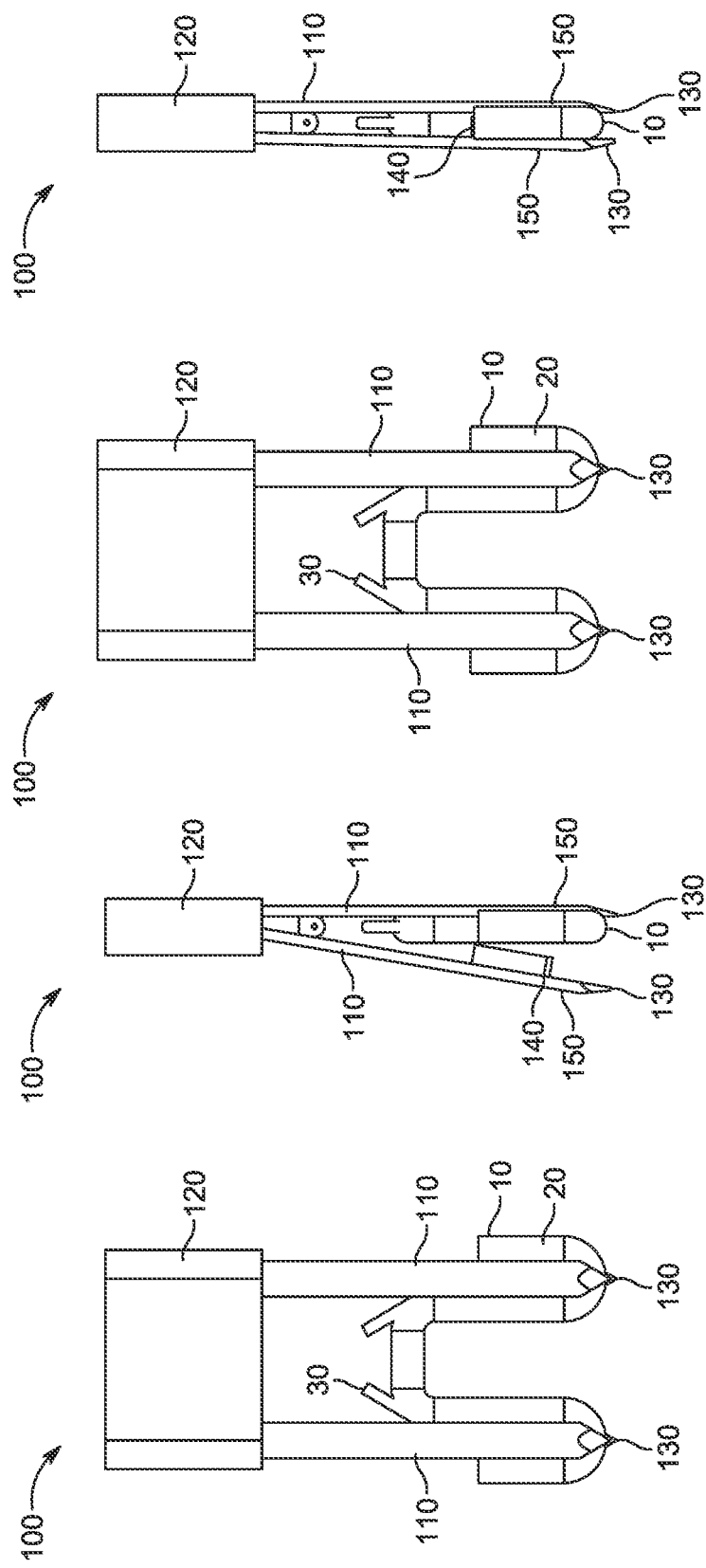

SURGICAL SHEATH, STAPLE, AND SCAFFOLD BONE ANCHOR DEVICES

BACKGROUND

1. Field of the Invention

The present invention relates generally to surgical bone sheath stable devices, bone sheath anchors, scaffolds integrating sheath anchors, and methods of use, and more specifically, to a staple sheath anchor that directly or indirectly affixes soft tissue (e.g. tendons, ligaments, etc.) to bone. Embodiments of the invention involve bone sheath staples that directly secure and compress soft tissue to bone. Embodiments of the invention also involve bone sheath anchors that integrate a suture with a sheath such that tension is applied to the suture to shape the sheath in an expanded orientation to engage a bone channel and lock the sheath suture anchor to bone. The anchors can then be used to secure soft tissue into engagement with bone. Embodiments of the invention further facilitate placement of scaffolds to bone by integrating or coupling sheath anchors into the scaffold. The sheath staples, anchors and/or scaffolds may incorporate a suture or features that pass suture to augment the affixation of soft tissues to bone. The sheath anchors can be used in either open or arthroscopic procedures. The sheath anchors are available in different sizes, which allow the attachment of soft tissues to bones of different sizes and for different applications.

2. Description of Related Art

One need in orthopedic surgery is the secure attachment of soft tissues to bones. Bone anchors are commonly used to secure suture to bones where the suture can be passed through soft tissue such that when suture knots are tightened the soft tissue in positioned into engagement against the bone surface.

Providing a bone staple that directly engages soft tissue against bone to secure and compress the soft tissue into engagement against bone addresses key requirements for soft tissue fixation. Providing a bone sheath staple designed with at least one suture and at least one sheath avoids metal anchors and provides secure attachment and tailored compression to encourage healing of the soft tissue to bone. Stability is also provided between soft tissue and bone to ensure proper alignment during the healing process.

Bone sheath anchors that secure suture to bone so the suture can alternatively be used to engage soft tissue and secure the soft tissue to bone also benefits from an integrated suture and sheath anchor design. Providing a quick and atraumatic bone sheath anchor that secures suture to bone enables more stable attachment of soft tissue by creating double row, lateral row, or other types of soft tissue attachment. Alternatively, scaffolds may be integrated or coupled with bone sheath anchors or staples to facilitate secure attachment of the scaffolds to bone. These scaffolds, as well as the integrated or coupled anchor components, may be fabricated from biologically inert materials, bioabsorbable materials, nanofibers, or incorporate drugs, biologics, stem cells, other autologous or donor tissues, or other synthetic materials designed to enhance healing of soft tissue to bone attachments, improve stability of soft tissue to bone attachments, increase the integrity or performance of soft tissue, or other medically-indicated reason.

BRIEF SUMMARY OF THE INVENTION

The field of minimally invasive arthroscopic surgical techniques has rapidly progressed over the last decade and continues to evolve with new techniques and procedures performed through minimally invasive techniques. Rotator cuff surgery represents one of the most common orthopedic surgeries performed. A simple description of this surgery involves identifying the tear, debriding the bone and then securing the torn tendon to the bone providing greater tuberosity. This is almost universally done with the use of suture anchors. The anchor is typically a screw that may be screwed within a pilot hole or impacted into the bone.

Extending out of the anchor are sutures that are individually passed through the tissue and then tied down to secure the tendon to bone. This process can be complex depending on training, experience and tear pattern. In addition, it can be a time-consuming process passing sutures individually and tying them to secure soft tissue against bone. Multiple needle passages can be traumatic to already torn and degenerated tissue. Proper tension/compression is not always achievable with sutures. There is also the issue of "knot security". Knots can become undone or loose.

The objectives of the device provide a staple device or anchor fabricated from at least one suture and at least one sheath. Through the devices, a skilled surgeon can quickly and efficiently secure the rotator cuff to the bone in a one to two step process. A suture will be passed through the tendon and then through the device for proper positioning and tension. Once appropriate, the tendon is secured to bone through the use of a sheath staple that is impacted through the tendon and into bone. The sheath staple will be small enough to limit excess bone and tissue loss and trauma but large enough to provide enough strength and compression. The sheath staple may include features to increase further pull-out tensile force or attachment strength. A sheath anchor may alternatively be used to secure suture to bone so the suture can subsequently be passed through soft tissue so suture knots can be tied to attach the soft tissue to bone. The sheath staple, sheath anchor and/or sheath anchor integrated scaffold devices may be made of polymer sheath material, fiberwire, braided, woven or other geometry of suture or biological textile material, bioabsorbable polymers and/or other biocompatible material with appropriate mechanical properties, or a composite of such materials.

The sheath staple and/or suture anchor may also be integrated to scaffolds that are infused, embedded, or otherwise incorporate collagen, stem cells, drugs, biologics, other autologous or donor tissue, other medicinal substances, or other material to encourage healing and/or reduce stress on the soft tissue. This technology can be applied to all areas of surgery that use suture anchors to secure tissue to bone e.g., labral repairs, ligament repairs and reconstruction. This will greatly decrease surgical time and improve ease of use. It may also lead to increased rates of healing.

The various embodiments of the present invention provide a variety of integrated bone staple devices that affix soft tissue to bone, apply tailored compression between soft tissues and bone, or better enable reinforced attachment of soft tissue to bone such as double row or lateral row fixation.

The various embodiments incorporate bone sheath staple implants, sheath anchors, scaffolds that integrate or couple at least one sheath staple or anchor, deployment systems that inserts the implants, and sheath staple and/or anchor features that better atraumatically affix soft tissue to bone at the insertion sites.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

FIGS. 6A to 6C show side-sectional views of three elongated sheath scaffold embodiments that integrate bone sheath anchors by incorporating at least one suture tightening member to at least one distal end member of the scaffold to facilitate attachment of at least one end of the scaffold within at least one bone channel.

FIGS. 10A to 10B show a side view and an end view of a deployment system in an open orientation to place a bone sheath staple, which may also be modified to insert a sheath anchor or sheath scaffold anchor, to prepare for insertion of the distal end members of the sheath staple or anchor, into a bone channel to secure the staple, anchor, or scaffold to bone.

FIGS. 11A to 11B show the system in FIGS. 10A to 10B in a closed position that is prepared to deploy the staple, anchor, or scaffold into a bone channel by tapping to create a bone channel and simultaneously inserting the distal end members of the sheath staple or anchor.

Figure 1:
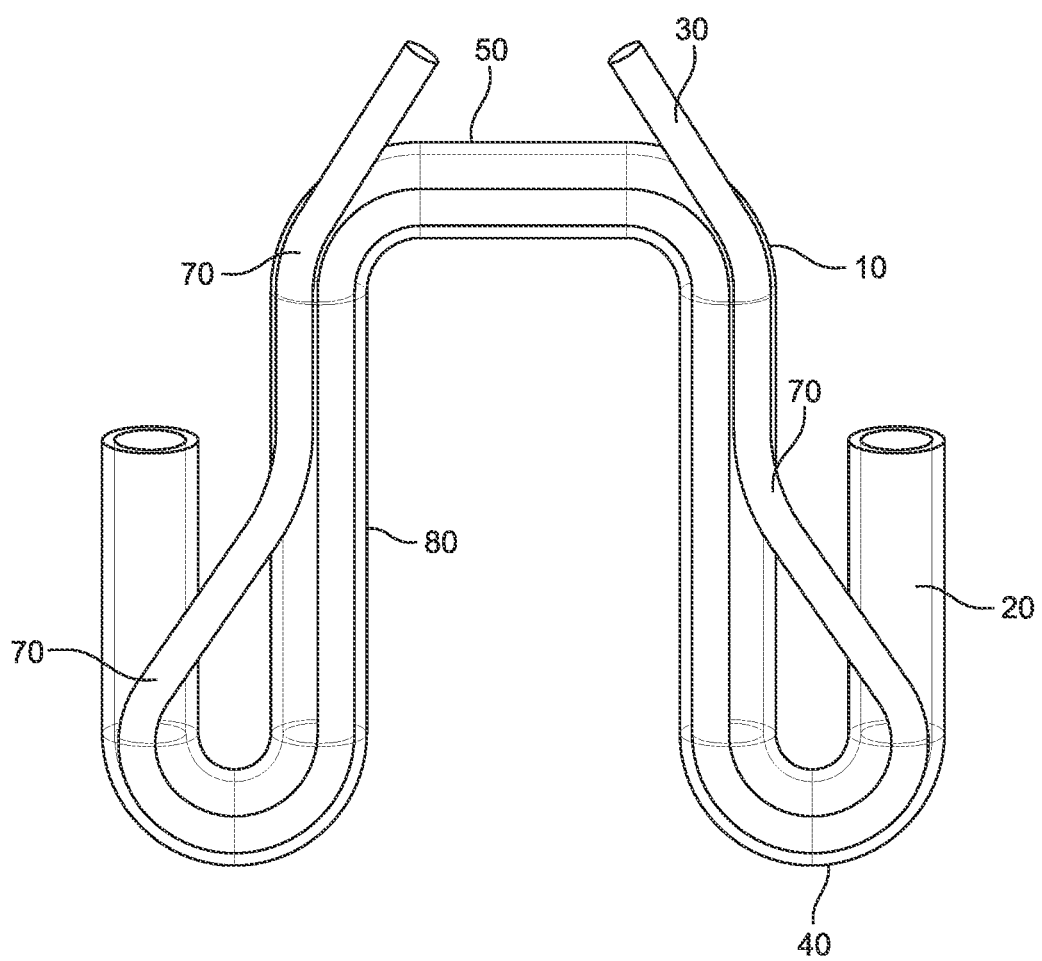
FIG. 1 shows a side view of a bone sheath staple embodiment that incorporates a suture tightening member that actuates the distal end members of the sheath within bone channels to directly secure soft tissue to bone.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional bone staple and anchors. Specifically, the invention of the present application provides a non-invasive and efficient method of joining ruptured or damaged soft tissue to bone to facilitate their healing. This and other unique features of the system and methods of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

The bone staple and anchor embodiments included in this application present improvements to increase functionality and clinical utility for embodiments in pending patent application Ser. No. 15/973,303 entitled "Surgical bone staple device and method of use" and Ser. No. 17/332,612 entitled "Surgical bone stable device and method of use", the contents of these documents are hereby incorporated by reference as if recited in full herein.

Referring now to the drawings wherein like reference characters identify corresponding or similar elements throughout the several views, FIGS. 1-11 depict several embodiments of the invention of the application. It should be understood that the embodiments discussed herein are substantially similar in form and function and share one or more of the features discussed in each embodiment although the features may not be shown specifically with reference to the particular embodiment.

FIGS. 1-2 depict a bone sheath staple device 10 embodiment exemplified by this disclosure. The bone sheath staple 10 directly secures soft tissues to bone without using individual suture anchors, allowing a surgeon to institute placement of a fastener to retain the soft tissue on an underlying bone with minimal damage to the soft tissue or the bone. Several embodiments of the bone sheath staple device are contained within this disclosure.

The bone sheath staple device 10 includes two or more parallel legs 80 that include distal end members 40 that are actuated into a deformed, expanded, or otherwise secure orientation upon penetration through soft tissue and into bone channels during insertion of the bone sheath staple. The legs 80 include the distal end members 40 that are actuated by retraction of at least one integrated suture tightening member 30 to secure the distal end members 40 into bone channels to increase pull-out force and better ensure tensile strength of the secured soft tissue to bone attachment.

The embodiments of the invention incorporate at least one sheath 20 made of polymer strands braided, woven, or otherwise fabricated into a tubular mesh or other elongated geometry that incorporates the parallel legs 80 and the distal end members 40 that may be tapped into a bone channel such that actuation of suture tightening member 30, which is coupled to the sheath 20 and passes through side wall puncture sites 70 to cause actuation of the parallel distal end members 40 to deform, expand, or otherwise engaged within the bone channel to secure to the sheath staple, thus the encapsulated tendon, to bone thereby ensuring attachment between the sheath staple, tendon, and bone.

As FIG. 1 shows, the bone staple device 10 in some embodiments combines a single suture tightening member 30 and a single sheath 20 to secure tendon or other soft tissue directly to bone. A single sheath 20 of polymer strands woven or otherwise fabricated into a mesh, braid, or other tubular, ribbon, or alternative elongated geometry has ends that are heat treated, glued, molded, or otherwise stabilized to avoid unraveling of the sheath 20 during or after deployment.

A single suture tightening member 30 in some embodiments, consists of a 2-0 fiber-wire, polyester, PTFE, or other strong suture material is fed through the sheath 20 such that the middle portion resides within the base 50 of the sheath while the opposite ends pass through side wall puncture sites 70 of the sheath 20 to define and/or actuate distal end members 40 of the sheath 20. The suture tightening member 30 is fed back through the side wall puncture sites 70 of the sheath 20 while exiting just before the base 50 of the bone sheath staple. The free ends of the suture tightening member 30 may be pre-tied into a knot such that once inserted, retraction of one or more free ends of the suture tightening member 30 causes the distal end members 40 to deform, expand in diameter, or otherwise engage the bone channel through which the distal end members 40 of the bone sheath staple 10 were tapped. Once full engagement of the distal end members 40 of the bone sheath staple 10 within the bone channel has been obtained, the pre-tied knot maintains the bone sheath staple in the attached orientation and the free ends of the suture tightening member 30 may be used to tie to other bone sheath staples or anchors to affect a double row anchor, a lateral row anchor, or may otherwise be passed through other tendons, ligaments, and/or muscle to affix those soft tissues to the bone sheath staple.

Figure 3A:
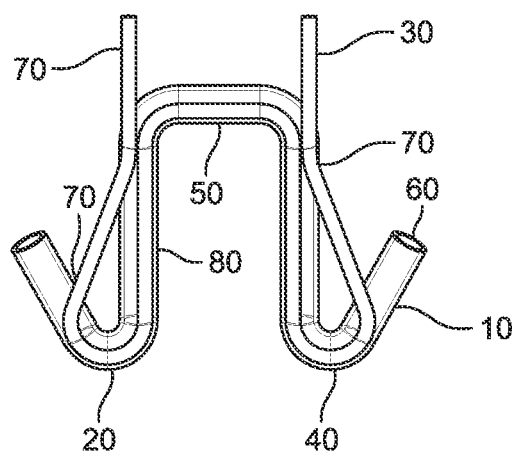
FIGS. 3A to 3E show side-sectional views of two bone sheath staple embodiments that incorporate at least one suture tightening member that actuates the distal end members of the sheath within the bone channels to secure the sheath staple to bone.
Figure 3B:
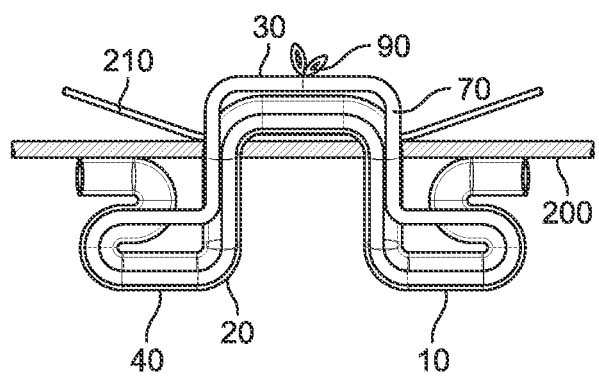

FIG. 3A shows the bone sheath staple 10 embodiment of FIG. 1 in a non-deployed orientation. FIG. 3B shows the bone sheath staple 10 of FIGS. 1 and 3A in an actuated orientation where the distal end members 40 have been inserted through tendon or other soft tissue 210 and into a channel through bone 200. Once inserted into bone channels, the distal end members 40 are actuated by retraction of the free ends of the suture tightening member 30 to deform, expand, or otherwise engage the distal end members 40 within the bone channel. The free ends of the suture tightening member 30 are tied into a knot 90 to maintain the actuated orientation of the distal end members 40.

Figure 3C:
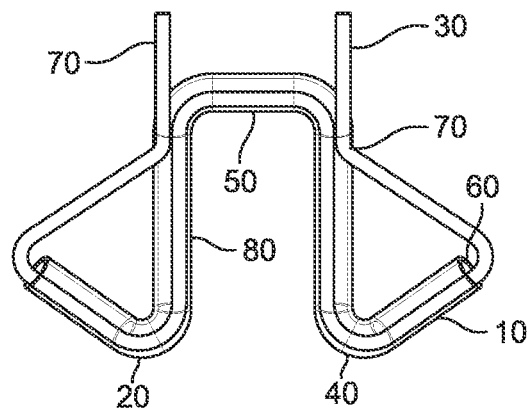
Figure 3D:
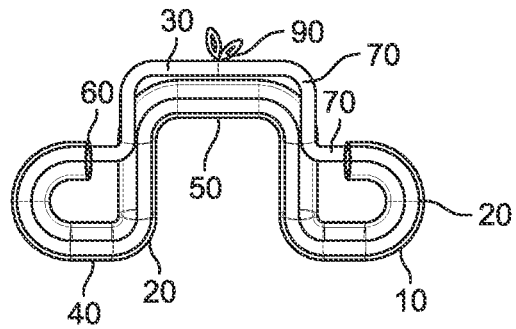
Figure 3E:
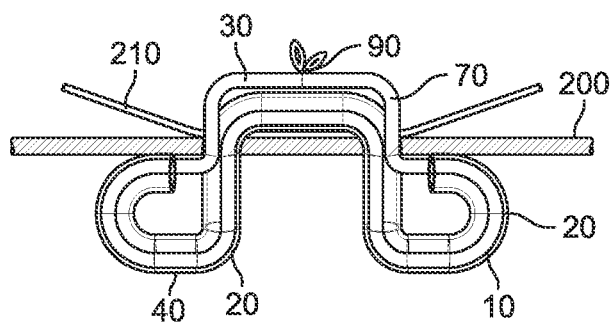

FIG. 3C shows an alternative bone sheath staple 10 embodiment where the suture tightening member 30 is passed through the sheath ends 60 before passing through the side wall puncture sites 70. FIG. 3D shows the bone sheath staple 10 of FIG. 3C in an actuated orientation. FIG. 3E shows the actuated bone sheath staple 10 of FIG. 3D with tendon or other soft tissue 210 compressed against bone 200 after the distal end members 40 are secured within the bone channels.

It should be noted that the free ends of the sheath staple may alternatively be secured to the sides of the sheath legs 80 at the locations where the suture strands pass back into the legs 50 of the sheath 20 past the distal end members 40 and before they exit the base 50 from where they can be tied. It should also be noted that more than one suture tightening member 40 may be incorporated in the sheath 20 to enhance deformation, enlargement, or otherwise engagement of at least one distal end member 40 within at least one bone channel or in the presented embodiment, parallel distal end members 40 within two parallel bone channels.

Figure 2B:
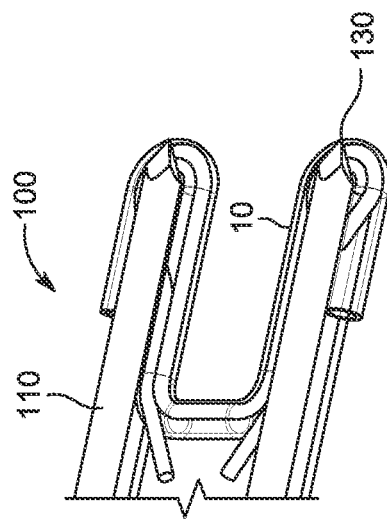
FIGS. 2A to 2C show a side view, a perspective view, and an end view of a deployment system for the bone sheath staple embodiment of FIG. 1.
Figure 2C:
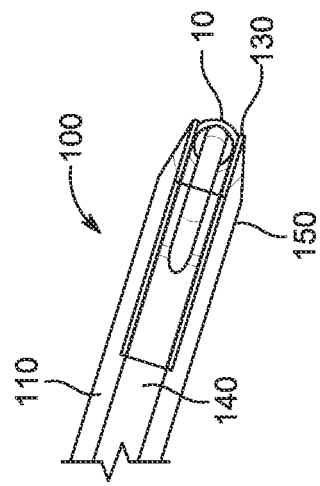
Figure 2A:
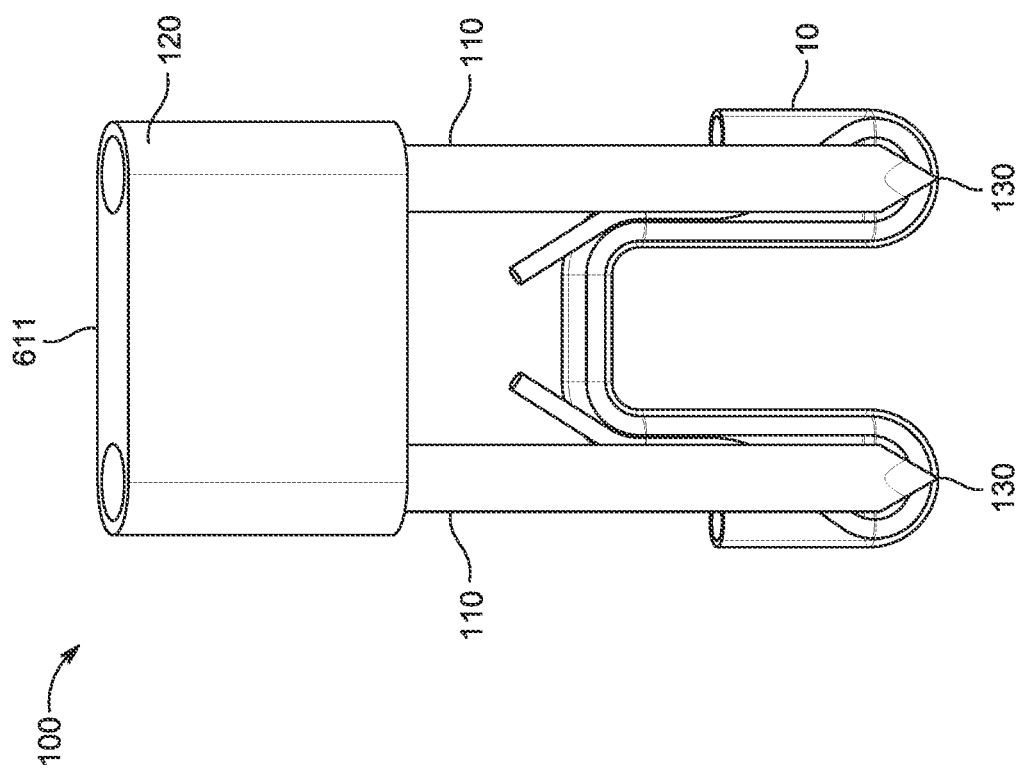

FIG. 2A to 2C show a deployment system 100 that is used to tap the distal end members 40 of the bone sheath staple 10 into bone by creating bone channels and inserting the distal end members 40. The deployment system 100 creates parallel bone channels into which the distal end regions 40 can be inserted and activated by tightening of the bone sheath staple suture member 30 to secure the staple to the bone. Prior to tapping the bone sheath staple into bone, the deployment system 100 is used to pass the distal end members 40 of the bone sheath staple 10 through tendon or other soft tissue.

Once the deployment system 100 is used to create a bone channel while simultaneously inserting the distal end members 40 of the sheath staple 10 into the tapped bone channels, the suture tightening member 30 free ends are retracted causing the distal end members 40 to deform, expand, or otherwise engage the bone channel thereby securing the bone sheath staple 10 to the bone. This deployment process simultaneously secures the bone sheath staple 10 to bone and compresses the tendon or other soft tissue 210 between the base 50 of the bone sheath staple and bone 200.

It should be noted that pre-drilled bone channels may be created to facilitate insertion of the distal end members 40 into the bone channels prior to actuation of the at least one suture tightening member 30 which deforms, expand, or otherwise engages distal end members 40 within the bone channels.

It should be noted that a one way valve involving a stiff polymer with features that allow the ends of the suture tightening member 30 to pass only one way may be used in lieu of pre-tied knot to secure the suture in the retracted, tightened orientation thus maintaining the bone sheath staple in the actuated/attached orientation.

The deployment system 100, as shown in FIG. 2A to 2C, includes an active housing 120 with two parallel supports 110 that each incorporates two penetrating needles 150 that include sharp ends 130 capable of penetrating bone to create the bone channel. The penetrating needles 150 support the distal end regions 40 of the sheath staple 10 during insertion into bone channels. Each set of penetrating needles 150 includes a distal slot 140 between the sharp ends 130 for the distal end regions 40 of the bone sheath staple 10 to reside while inserting through the bone channel. The sharp ends 130 of the penetrating needles 150 define cutting or dilating features so as to create a channel into bone while the operator applies impact force against the deployment system base 120 to tap the bone sheath staple 10 distal end members 40 into channels created in bone by the penetrating needles 150. Each set of penetrating needles 150 may be fabricated from separate components that are connected together or a single needle that includes a central cut-out 140 within which the distal end regions 40 of the bone sheath staple 10 resides during deployment.

The deployment system may include a stabilizing bar to support the base 50 of the bone sheath staple, thus the captured tendon or other soft tissue, during deployment. Once the deployment system taps the penetrating needles 150 into bone, creating two parallel bone channels within which the distal end members 40 of the sheath 20 are simultaneously inserted, the penetrating needles 150 are retracted while the free ends of the suture tightening member 30 are used to actuate the distal end members 40 while the stabilizing bar maintains the orientation of the base 50 to ensure the bone sheath staple 10 does not move while the suture tightening member 30 is actuated to secure the distal end members within the bone channels.

FIGS. 10A and 10B show an alternative deployment system 100 that includes a loading orientation to insert the bone sheath staple 10 prior to deployment. Once the bone sheath staple 10 is positioned between the penetrating needles 150 of the parallel supports 110 and abuts the stabilizing base at the cut-out slots 140, the parallel supports 110 and associated penetrating needles 150 of the deployment system 100 are closed for deployment as shown in FIGS. 11A and 11B.

It should be noted that the deployment system 100 embodiments above may alternatively incorporate a single support 110 coupled to the housing 120 that includes the penetrating needles 150. In this alternative embodiment, the deployment system with a single set of penetrating needles 150 is configured to insert a single distal end member 45 of a bone sheath anchor 15 into a bone channel as will be discussed below.

Figure 4A:
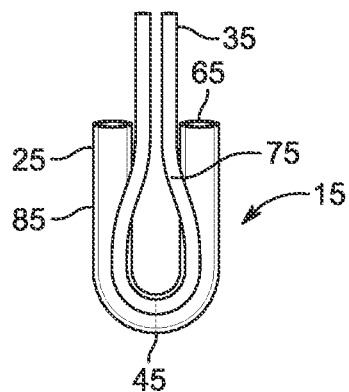
FIGS. 4A to 4H show side-sectional views of four bone sheath anchor embodiments with differing suture tightening member configurations that cause the at least one distal end member of the sheath to deform, expand and/or otherwise engage the at least one bone channel to secure the sheath anchor to bone.
Figure 4B:
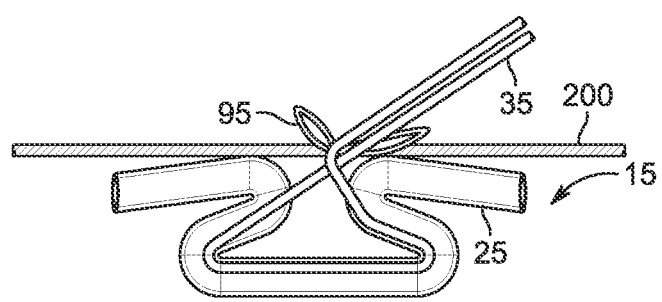

FIG. 4A shows a bone sheath anchor 15 embodiment of the invention that consists of a single sheath 25 with a single suture tightening member 35 that passes through the side wall puncture sites 75 on opposite sheath legs 85 to define a single distal end member 45 that deforms, expand, or otherwise engages a bone channel upon tightening of the suture member 35 free ends and tying into a knot 95 as shown in FIG. 4B.

Figure 4C:
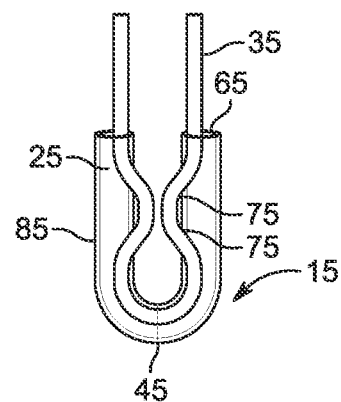
Figure 4D:
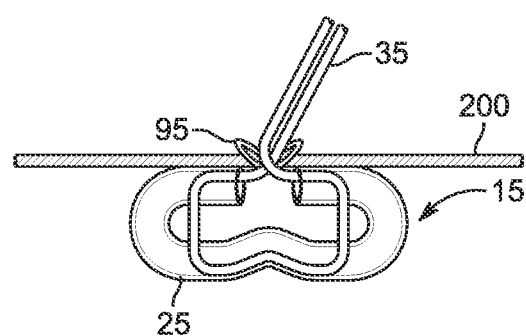

FIGS. 4C and 4D show non-deployed and actuated orientations for an alternative bone sheath anchor 15 embodiment of the invention. This bone sheath anchor 15 embodiment passes the suture tightening member 35 through the sheath ends 65 and inward through side wall puncture sites 75 and back through the lumen of the sheath along the distal end member 45 to define a different actuation orientation as shown in FIG. 4D.

Figure 4E:
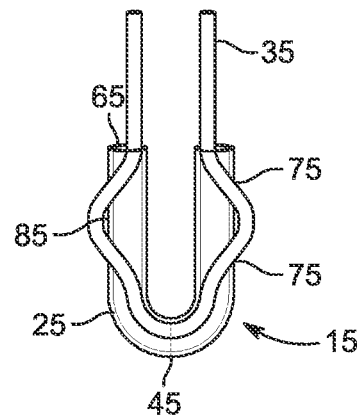
Figure 4F:
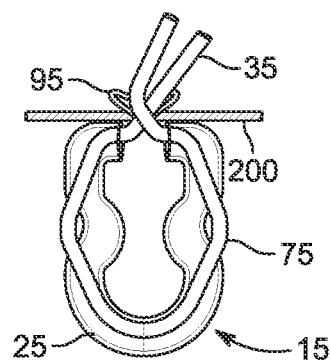

FIGS. 4E and 4F show non-deployed and actuated orientations for another bone sheath anchor embodiment 15 where the suture tightening member 35 passes outward through the side wall puncture sites 75 so the sheath bunches upon tightening of the free suture member 35 ends.

Figure 4G:
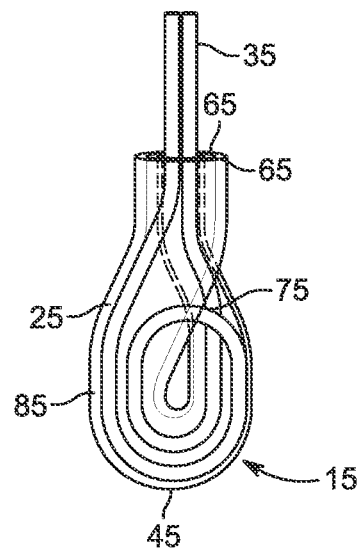
Figure 4H:
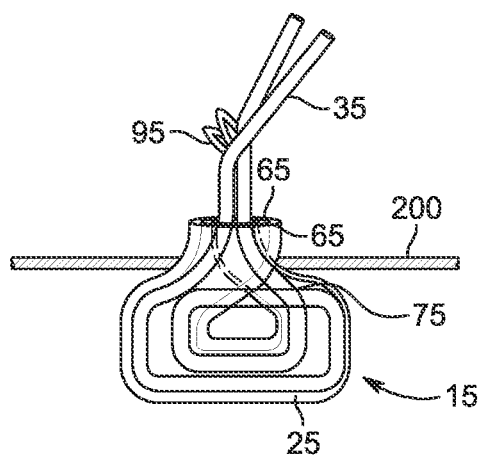

FIGS. 4G and 4H show non-deployed and actuated orientations for another bone sheath anchor embodiment 15 where one sheath end 65 is inserted through the side wall of the sheath 25 and abuts the other sheath end 65. The suture tightening member 35 is wound around the loop defined by the sheath after passing through the side wall puncture sites 75 and the free ends of the suture tightening member 35 pass through the sheath ends 65.

Figure 5A:
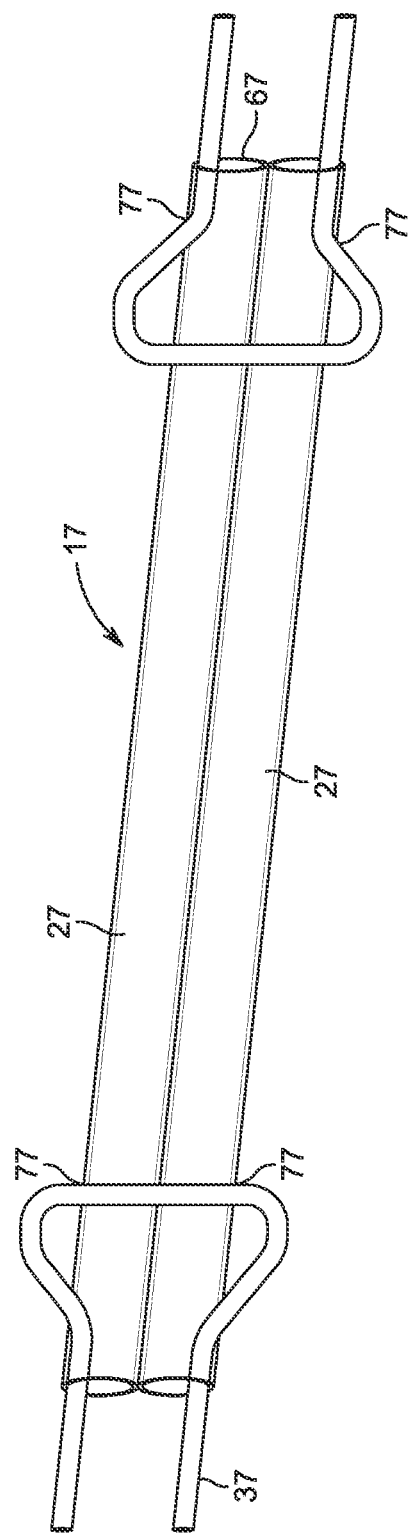
FIGS. 5A to 5B show a top-sectional view and a side-sectional view of an elongated ribbon sheath scaffold embodiment that integrates bone sheath anchors by incorporating at least one suture tightening member coupled to at least one end of the scaffold that facilitates attachment of at least one distal end member of the scaffold within at least one bone channel.
Figure 5B:
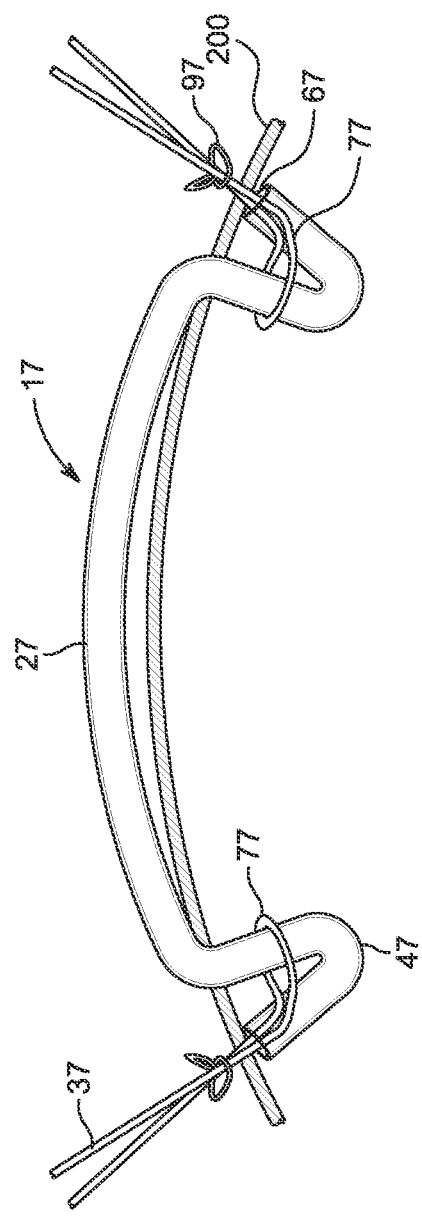

FIG. 5A shows a scaffold 17 fabricated from a ribbon with parallel tubular sheath members 27 capable of defining a structure to which tendon or other soft tissue can better heal to bone 200. Suture tightening members 37 are positioned at each end of the scaffold through the sheath ends 67 and side wall puncture sites 77 to loop through the sheath members 27 and define distal end members 47 thus scaffold anchors that can be actuated upon insertion of the distal end members 47 into bone channels and actuation of the suture tightening members 37 as shown in FIG. 5B.

Figure 9:
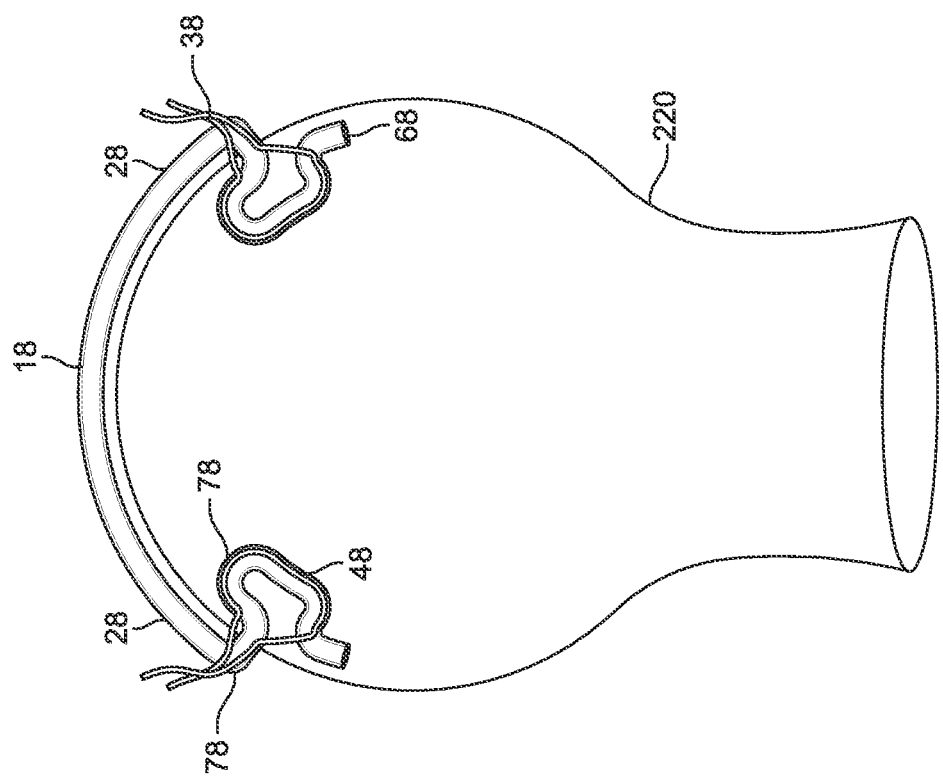
FIG. 9 shows a side sectional view of a scaffold embodiment attached to bone by actuation of sheath anchors incorporated or coupled to the scaffold.

FIGS. 6A to 6C show three alternative sheath scaffold 18 embodiments that integrate sheath anchors into the sheath 28. The sheath scaffold 18 embodiment in FIG. 6A includes suture tightening members 38 that define distal end members 48 by passing through the sheath ends 68 and looping through the side wall puncture sites 78. Once the distal end members 48 are inserted into bone channels and the suture tightening member 38 is actuated, the distal end members 48 are secured within the bone channel to secure the sheath scaffold 18 in place as shown in FIG. 9.

The sheaths 28 of the scaffold embodiments may incorporate complex geometries where the tubular ends are flattened between the integrated sheath scaffold anchors to define anchor regions and bone scaffold regions.

FIG. 6B shown an alternative sheath scaffold 18 embodiment where two suture tightening members 38 pass through the entire length of the sheath 28 and pass through side wall puncture sites 78 to define the distal end members.

FIG. 6C shows an alternative sheath scaffold 18 embodiment where the suture tightening members 38 are passed through side wall puncture sites 78 and wound into a complex orientation within the sheath lumen to enhance the deformation, expansion, or otherwise engagement of the distal end members within bone channels.

Figure 7B:
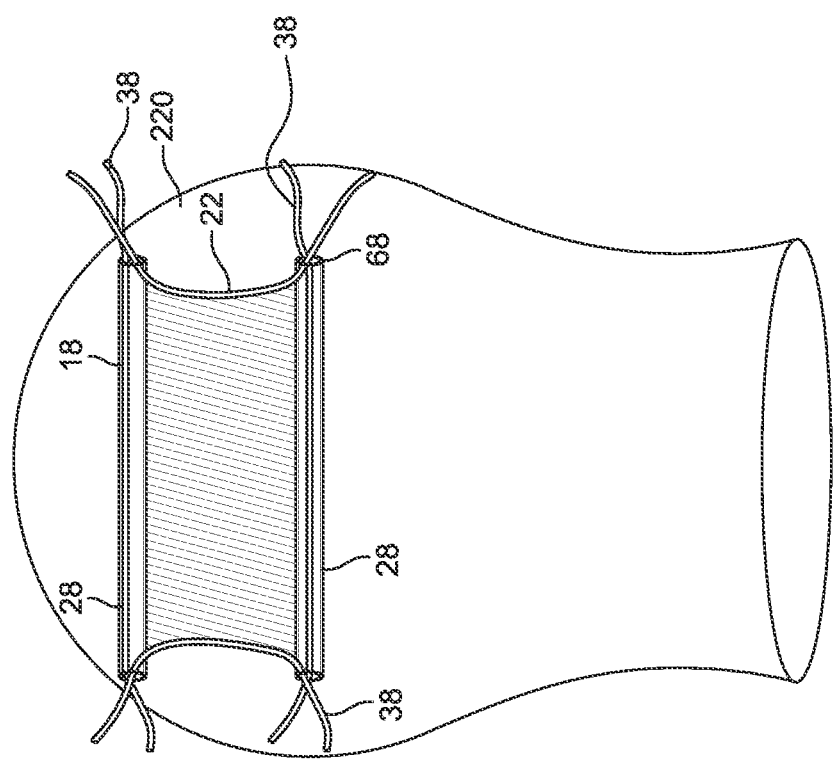
FIGS. 7B to 7D show end views of three scaffold embodiments that integrate mesh or other textile support sheets with sheath support members that integrate sheath anchors to facilitate attachment of the scaffolds to bone.
Figure 7A:
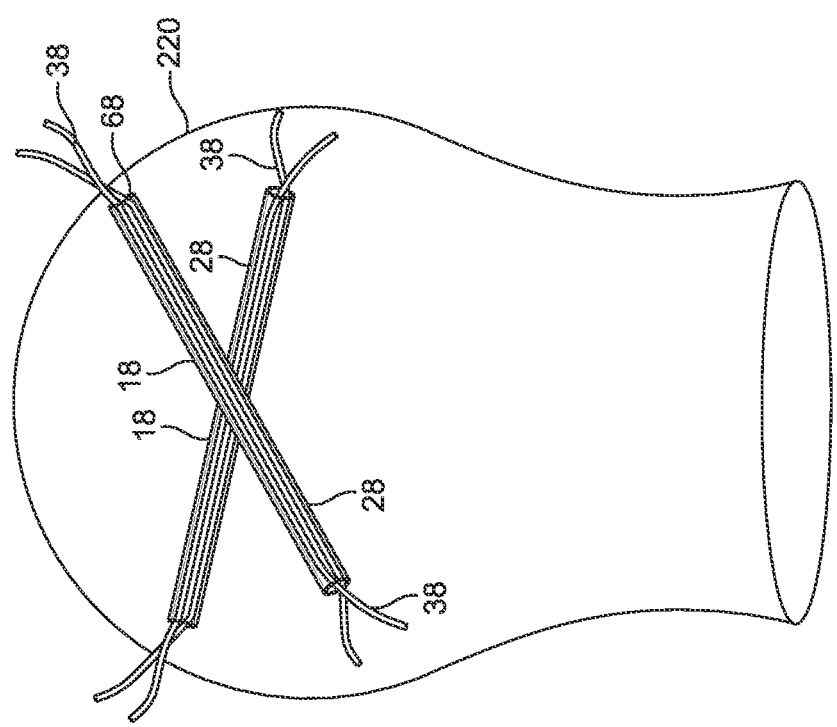
FIG. 7A shows an end view of a scaffold embodiment that incorporates multiple individual scaffold support members, each attached to bone with integrated sheath anchors.

The sheath scaffolds 18 above may be secured to bone in various configurations including the crossing pattern shown in FIG. 7A. Alternative patterns may alternatively be created to provide a scaffold to which tendon or other soft tissue can be secured to promote stability and healing to bone 220.

Figure 7D:
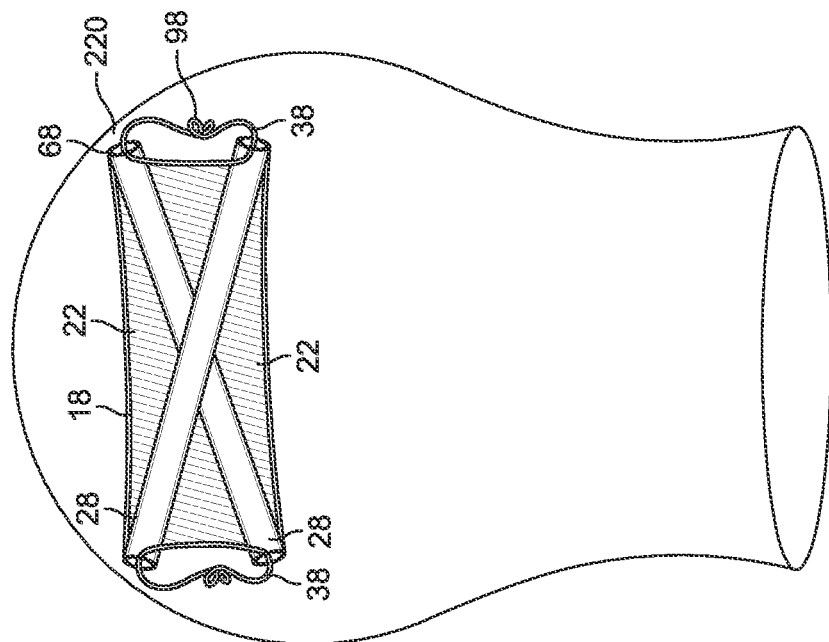
Figure 7C:
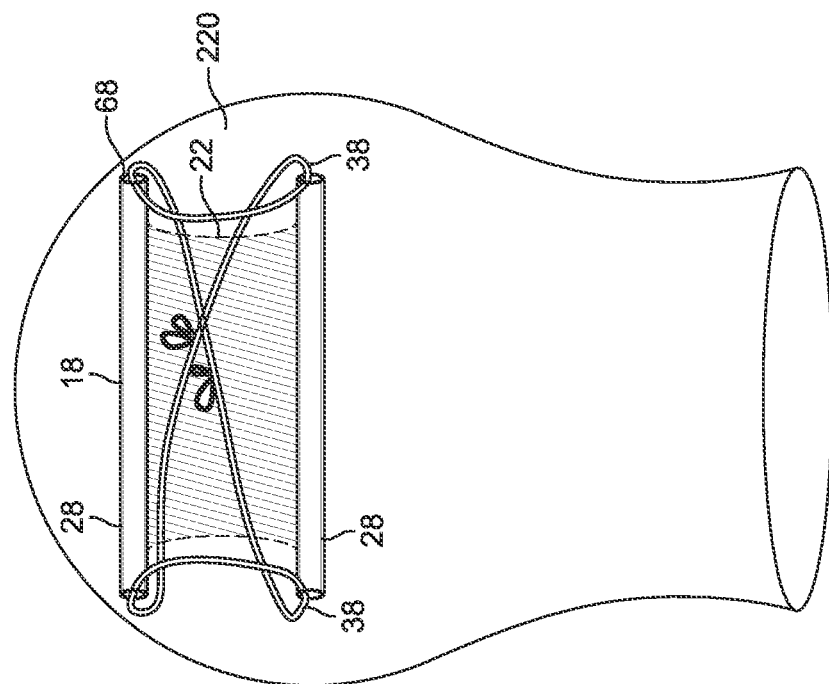

The individual scaffold sheaths 28 may support a mesh or sheet members 22 that can be secured to bone 220 by insertion and attachment of the scaffold anchors into bone channels as shown in FIG. 7B. Alternative scaffold configurations with scaffold sheaths 28 that support mesh or sheet members 22 are shown in FIGS. 7C and 7D.

Figure 8A:
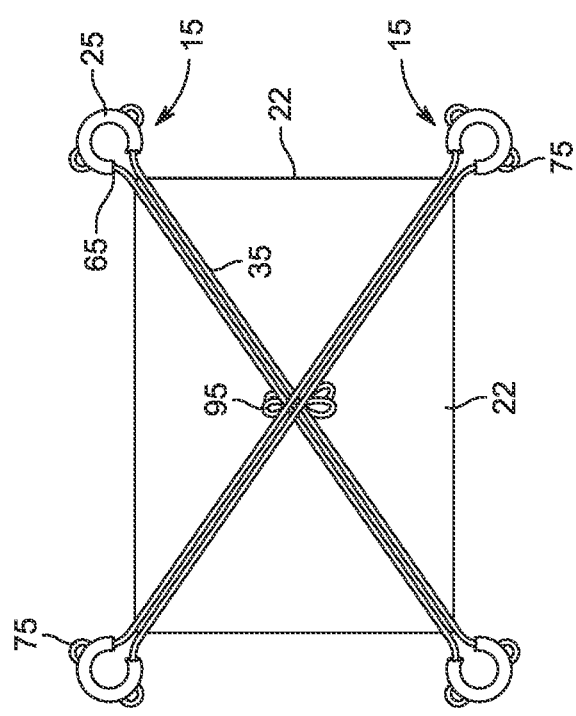
FIGS. 8A to 8B show top views of a sheet scaffold that incorporates individual sheath anchors that attachment the scaffold to bone.
Figure 8B:
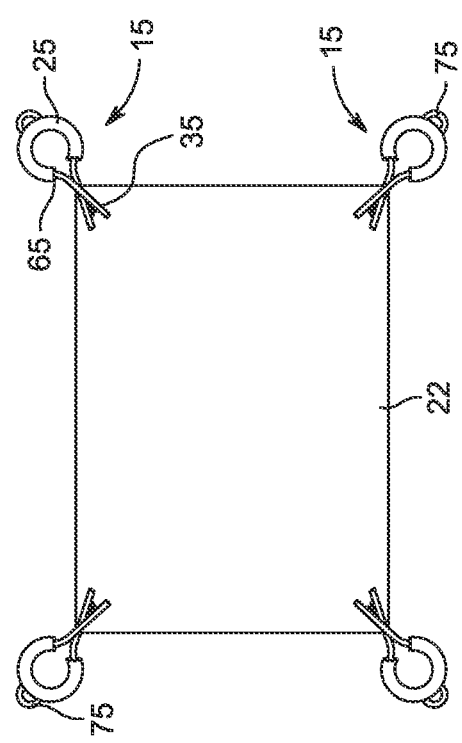

FIGS. 8A and 8B show alternative scaffold embodiments that incorporate sheath anchors 15 as described previously. The sheath anchors 15 are tapped into bone and secured within the bone channels to secure the mesh or sheet member 22 to bone 220. The free ends of the suture tightening members 35 may be subsequently tied into knots 95 to further reinforce position of the scaffold against bone and to facilitate attachment of tendon or other soft tissue to the scaffold and bone.

The bone sheath staple devices, anchors, and scaffolds shown are merely representative of several variations and embodiments of the invention. It is not the intent to limit the scope of the staples, anchors, scaffolds, and instruments used to insert the staples or anchors into bone channels, nor to limit the use of the staples, anchors, or scaffolds to rotator cuff repairs. It is ideal for rotator cuff repairs, but surgeons may choose to use the staples for other soft tissue and other bone attachments.

The sheath staples are also not limited to two prong embodiments and may utilize one staple leg or a plurality of staple legs, with or without sheaths or other features, and in configurations not necessarily linear, including a triangular configuration, a square configuration or a polygon, with more than one bridge between the staple distal end members or in a geometrical design suitable for the tissue repairs.

The staples, anchors, and scaffolds may be deployed by other apparatuses, although a hard contact implement is not recommended due to the risk of penetration of the soft tissue, deformity or damage to the soft tissue or bone. The staples, anchors, and scaffolds may be made of metal, thermoplastic, nitinol, suture material, silicone, urethane, PTFE, nylon, other polymer, other biocompatible and bioabsorbable material, or a combination of materials use in implant devices. In addition, coverings may be placed over sections of the bone staples, anchors, and scaffolds to reduce stresses on soft tissue, further encourage healing, or other purpose that enhances the secure attachment of soft tissue to bone. Although the embodiments of the have been described and shown above, it will be appreciated by those skilled in the art that numerous modifications may be made therein without departing from the scope of the invention as herein described.

While various orthopedic applications benefit from the use of bone staple anchor embodiments of the invention, rotator cuff tendon repair (e.g. partial or complete tears) is one illustrative example that will be described in more detail. The rotator cuff tendon tear is identified and the tendon is debrided. The tuberosity insertion site is likely decorticated. The tendon is approximated to its insertion site. Through percutaneous techniques, arthroscopic cannulas or open approaches the tendon is secured down to the footprint by insertion of the bone sheath staple device into the tendon and then into the bone.

Proper distal end member deployment and resistance to pullout is confirmed by pulling on the device the inserter or sutures that run through it. This device may be used with or without sutures. Suture tightening members are integrated within the staple, anchor, and/or scaffolds as shown in the embodiments above. The bone sheath staples, anchors, and/or scaffolds may then be used to create a double row construct by placing lateral to the initial staple or anchor. It may also be placed medial or lateral to the initial staple or anchor. It should be noted that any number of bone sheath staples, anchors, and/or scaffolds may be utilized to ensure proper placement and attachment of soft tissue to bone.

Other applications that benefit from the bone sheath staple, anchor, and/or scaffold embodiments of the invention include biceps tenodesis where the short head or long head of the biceps tendon is secured to the groove, total shoulder arthroplasty where the subscapularis tendon is repaired, attaching grafts when performing procedures such as superior capsular reconstruction, securing grafts to the glenoid, fixing the anterior cruciate ligament, repairing the medial and/or lateral collateral knee ligaments or any application requiring the attachment of soft tissue to bone.

The staple, anchor, and/or scaffold embodiments of the invention may alternatively include securing triceps tendon, achilles tendon, patella tendon, or quadriceps tendon to bone. The embodiments of the invention may also help support ligaments including ankle ligaments (e.g deltoid ligament), knee ligaments (e.g anterior cruciate ligament), elbow ligaments (e.g ulnar collateral ligament), shoulder ligament (e.g glenohumeral ligament), hip ligaments, and ligaments of the hand and wrist. The embodiments may be used in conjunction with elective or non-elective procedures for lateral collateral ligament repair in elbow instability surgery. The embodiments may be used to aid fracture repair by providing provisional fixation across the fracture fragments. The embodiments may be used to facilitate fixation of biologic augments and grafts including autograft tendons used for healing, cadaveric tendons allograft used to facilitate healing, cadaveric tendon allograft used to increase structural support, autograft tendon used to facilitate healing, human dermal allografts, all grafts used in superior capsular reconstructions of the shoulder, and augmenting soft tissue repair with synthetic, cadaveric or autologous material.

To achieve the variety of applications, it is possible that the embodiments of the invention may manufactured at different dimensions. In addition, the deployment mechanism may be altered to facilitate access and use in different body parts.

The bone sheath staple, anchor and/or scaffold embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A bone sheath staple device, comprising:
 a sheath having:
   a first leg having a first distal end member;
   a second leg having a second distal end member;
   a suture tightening member engaged with the first distal end member and the second distal end member;
   wherein the first leg and the second leg pass through soft tissue prior to insertion into bone;
   wherein tension applied to the suture tightening member retracts the first distal end member and the second distal end member to increase pull-out force; and
   wherein the bone sheath staple device is configured to secure soft tissue to bone.

2. The device of claim 1, wherein the sheath further includes:
 a first puncture site through the sheath;
 wherein the suture tightening member extends through the first puncture site.

3. The device of claim 1, wherein the suture tightening device includes a first end and a second end and wherein each of the first and second ends are tied to create knots.

4. A bone sheath staple system, comprising:
 a bone sheath staple device, having:
   a sheath having:
     a first leg having a first distal end member;
     a second leg having a second distal end member;
     a suture tightening member engaged with the first distal end member and the second distal end member;
   a deployment system, having:
     a housing;

a first parallel support extending from the housing and to engage with the first leg; and a second parallel support extending from the housing and to engage with the second leg;

wherein the deployment system is configured to insert the first distal end member and the second distal end member into bone;

wherein force to the suture tightening member retracts the first distal end member and the second distal end member to increase pull-out force; and wherein the bone sheath staple device is configured to secure soft tissue to bone.

5. The system of claim 4, wherein the first parallel support includes a penetrating needle at a distal end of the parallel support.

6. A surgical scaffold, comprising:

a parallel tubular sheath, having a first tubular member and a second tubular member;

a first suture tightening member through a first end of the first tubular member and a first end of the second tubular member;

a second suture tightening member extending through a second end of the first tubular member and a second end of the second tubular member;

wherein actuation of the first suture tightening member actuates the first end of the first tubular member and the first end of the second tubular member;

wherein actuation of the second suture tightening member actuates the second end of the first tubular member and the second end of the second tubular member; and wherein the actuation causes the parallel tubular sheath to engage with a bone channel.

\* \* \* \* \*